United States Patent
Christensen (10) Patent No.: US 10,429,316 B2
(45) Date of Patent: Oct. 1, 2019

(54) METHOD AND DEVICE FOR SCANNING OF OBJECTS USING A COMBINATION OF SPECTRAL RANGES WITHIN VISION, NEAR INFRARED LIGHT AND X-RAYS

(71) Applicant: Teknologisk Institut, Taastrup (DK)

(72) Inventor: Lars Bager Christensen, Taastrup (DK)

(73) Assignee: Teknologisk Institut, Taastrup (DK)

( * ) Notice: Subject to any disclaimer, the term of this patent is extended or adjusted under 35 U.S.C. 154(b) by 0 days.

(21) Appl. No.: 16/069,455

(22) PCT Filed: Jan. 10, 2017

(86) PCT No.: PCT/EP2017/050382
§ 371 (c)(1),
(2) Date: Jul. 11, 2018

(87) PCT Pub. No.: WO2017/121713
PCT Pub. Date: Jul. 20, 2017

(65) Prior Publication Data
US 2019/0033227 A1   Jan. 31, 2019

(30) Foreign Application Priority Data

Jan. 11, 2016 (DK) ................................ 2016 00014
May 3, 2016 (DK) ................................ 2016 00271

(51) Int. Cl.
*G01N 21/88* (2006.01)
*G01N 33/02* (2006.01)
(Continued)

(52) U.S. Cl.
CPC ....... *G01N 21/8806* (2013.01); *A22C 17/008* (2013.01); *G01N 21/94* (2013.01);
(Continued)

(58) Field of Classification Search
CPC ............... G01N 21/8806; G01N 21/94; G01N 2021/845; G01N 2223/618; G01N 23/04;
(Continued)

(56) References Cited

U.S. PATENT DOCUMENTS

| 6,078,051 A | 6/2000 | Banton et al. |
| 2002/0067707 A1 | 6/2002 | Safai et al. |

(Continued)

FOREIGN PATENT DOCUMENTS

| WO | WO 02/43502 A2 | 6/2002 |
| WO | WO 2006/129351 A1 | 12/2006 |

(Continued)

*Primary Examiner* — Tri T Ton
(74) *Attorney, Agent, or Firm* — Holland & Hart LLP (57) ABSTRACT

The method and equipment described are for coherent scanning, that is where sections of the same object are comparable in the images, of objects such as food stuff based on scanning with the utilization of electromagnetic waves from at least two ranges within vision (visible light), NIR (near infrared light) and X-rays. The method consist of determination an object's reflection in the NIR and/or vision ranges associated with the same object's transmission in the X-ray range to obtain an even higher degree of details concerning the structure of the object by determining its surface texture together with description of its inner structure and/or composition. The equipment comprises a cabinet (2), a computer (6), a camera (3), an X-ray source (4), a light source (7), and an X-ray detector (5). An additional start sensor (8) registers the presence of objects on the conveyor belt (1) and the scanning is triggered.

13 Claims, 3 Drawing Sheets

(51) Int. Cl.
*G01N 21/94* (2006.01)
*G01N 23/04* (2018.01)
*G01N 23/083* (2018.01)
*A22C 17/00* (2006.01)
*G01N 33/12* (2006.01)
*G01N 21/84* (2006.01)

(52) U.S. Cl.
CPC ........... *G01N 23/04* (2013.01); *G01N 23/083* (2013.01); *G01N 33/02* (2013.01); *G01N 33/12* (2013.01); *G01N 2021/845* (2013.01); *G01N 2223/618* (2013.01)

(58) Field of Classification Search
CPC ...... G01N 23/083; G01N 33/02; G01N 33/12; A22C 17/008
See application file for complete search history.

(56) References Cited

U.S. PATENT DOCUMENTS

| | | |
|---|---|---|
| 2003/0072680 A1 | 4/2003 | Higuchi et al. |
| 2009/0080706 A1 | 3/2009 | Tao et al. |
| 2013/0293893 A1 | 11/2013 | Bonyuet et al. |
| 2015/0342202 A1 | 12/2015 | Grimm et al. |
| 2015/0377776 A1 | 12/2015 | Xie |

FOREIGN PATENT DOCUMENTS

| | | |
|---|---|---|
| WO | WO 2006/129391 A1 | 12/2006 |
| WO | WO 2008/102143 A1 | 8/2008 |

METHOD AND DEVICE FOR SCANNING OF OBJECTS USING A COMBINATION OF SPECTRAL RANGES WITHIN VISION, NEAR INFRARED LIGHT AND X-RAYS

The invention is related to a method and a device for scanning objects and is based on the use of more spectral ranges within vision, NIR and X-rays. Examining objects by the described scanning method can be used to control the quality of products such as to detect foreign bodies on and/or within the product such as in food products e.g. meat products.

BACKGROUND OF INVENTION

For food processing/producing and feed processing/producing companies as well as for other types of companies it is important that foreign bodies are not present in and/or on the products produced. However, it may be time consuming or impossible for humans to identify and remove all foreign bodies from products as the foreign bodies may be too small to be identified by humans or foreign bodies may be present within the products such as within minced or mixed products. Examples of foreign bodies in food and feed products are bone parts, plastic, metal, cardboard/paper, stones, and 'wrong species' such as separating different species from each other such as separating blue or common mussel (e.g. *Mytilus edulis*) from cockles (e.g. *Cerastoderma edule*). Foreign bodies in products reduce the quality and thus the value of the products. Foreign bodies in products may thus have economic consequences for a company.

Product value can also be determined based on an agreement between a producer and a customer in respect of the quality of the produced product. If the agreement determines e.g. a certain weight or number of an ingredient in a product, the quality and thus the value is reduced if the weight or number of this ingredient is too low. In this situation the producer may obtain a lower price than if the agreement was fulfilled. On the other hand the producer may have a 'give-away situation' if the weight or number of an ingredient is too high as this need not result in a higher price.

Systems for performing quality control of food by the use of reflected or transmitted light in the form of visible light and near-infra red light are described e.g. in WO 08/102143 ('Quality control of meat products using optical imaging') which describes an arrangement having first and second light sources and an imaging device. The light sources have different wavelengths. The first light source is positioned such that the imaging device is able to take images of an object under test that is backlit by said first source of light: the second light source is positioned such that the imaging device is able to take images of the object based on light reflected from the surface of said object. In use, the imaging device simultaneously generates a first image resulting from light provided by said first light source and a second image resulting from light provided by said second light source.

US2015/0342202 (Device and method for non-contact identifying of red tissue structures and assembly for removing a strip of red tissue structures) describes an apparatus and a corresponding method for non-contact identifying of red tissue structures in products of slaughtered animal bodies, comprising a conveying device for continuous conveyance of the products in a conveying direction, a light source configured to generate a flat light field which is designed and adapted to form a light line running transversely to the conveying direction of the product from the flat light field, a detecting device for identifying the red tissue structures, which comprises at least one optical sensor means for recording the portions of light reflected by the product, wherein the light source is configured as an infrared light source and the light source is arranged such that the plane of the flat light field relative to the conveying direction is tilted by a light field angle of less than 90°.

Control of products to obtain the requested quality is of utmost importance and as requirements to food quality increases fast and reliable systems and methods for performing quality control are required. The invention described herein makes it possible to perform quality control of products especially of food and feed products and especially in respect of detecting foreign bodies and for determining number of ingredients that vary in form or structure from the remaining product.

SUMMARY OF INVENTION

Quality control may be performed by scanning products to detect foreign bodies or other items which is present in too large amount or in too little amount. An equipment for performing such a scanning may comprise
- at least two sources for emitting electromagnetic waves selected among sources which can emit electromagnetic waves in a larger or narrower range and where the at least two sources emit electromagnetic waves with waves in different ranges and selected between the ranges
- 950 nm to 700 nm,
- 700 nm to 350 nm,
- 100 pm to 7 pm,
- Wherein at least one of the sources is capable of emitting electromagnetic waves within at least a part of the range 100 pm to 7 pm,
- and at least one sensor which can receive electromagnetic waves within part or the entire of at least one of the ranges
- 950 nm to 700 nm,
- 700 nm to 350 nm,
- 100 pm to 7 pm
- Wherein at least one of the sensors is capable of receiving electromagnetic waves within at least a part of the range 100 pm to 7 pm.

An equipment for scanning a product such as food or feed may comprise a conveyor belt for transporting products to be scanned, a cabinet enclosing the part of the electronic elements, sources for emitting electromagnetic waves such as light source(s), optionally an opening for light in the bottom part of the cabinet, sensor(s) for receiving electromagnetic waves such as camera(s), an X-ray source, optionally an opening for X-rays in the bottom part of the cabinet, an X-ray detector, a computer/processor, a start sensor for determining presence of a product on the conveyor belt, a control panel located outside of the cabinet e.g. mounted on the cabinet and connections between the electric components making the computer capable of controlling the sources and sensors and perform image analysis based on predetermined algorithms selected in respect of the product type being scanned.

The method may consist of determination of an object's reflection in the NIR and/or vision ranges associated with the same object's transmission within the X-rays range, in this way a greater level of details is obtained concerning the construction of the object by determining its surface texture together with a description of its inner structure and/or composition. The method uses generation of images at multispectral electromagnetic waves from at least two ranges within vision (visible light), NIR (near infrared light) and X-rays. It is hereby possible to apply:
- Multispectral vision+multispectral X-rays
- Multispectral NIR+multispectral X-rays
- Multispectral vision+multispectral NIR+multispectral X-rays where multispectral vision can be the entire or parts of the range 700 nm to 350 nm; multispectral NIR can be the entire or parts of the range 950 nm to 700 nm; multispectral X-rays can be the entire or parts of the range 100 pm to 7 pm.

The object which should be examined can be a defined physical item such as individual meat pieces, or it can be a continuous stream of material such as minced meat on a conveyor belt, however, other products can also be examined, preferred is examination of food and feed products. The method make use of establishing coherent measuring results e.g. in the form of coherent image data of reflection and/or transmission in the entire of the object's two-dimensional extent to be able to determine the composition of the object, including being able to scan the object for possible biological materials such as physical symptoms of disease. In respect of continuous streams of material such as minced products e.g. minced meat, the continuous stream of material which preferably is transported on an open conveyor belt is separated into imaginary sections of a predetermined length such that the generated coherent image data become of a size which reflects the predetermined imaginary section.

DETAILED DESCRIPTION OF THE INVENTION

The method and equipment/system described herein is for coherent scanning of objects such as of food and feed based on scanning with the use of electromagnetic waves from at least two ranges within vision (visible light), NIR (near infrared light) and X-rays. By 'coherent' is meant that in images obtained of an object, generated from electromagnetic waves from at least two ranges, sections of the same object area in the obtained images are compared. This analysis may be performed based on e.g. individual pixels of each image.

By combining spectral measurement of materials such as food or waste e.g. foreign bodies on/in food with electromagnetic waves within the ranges 950 nm to 700 nm, 700 nm to 350 nm and 100 pm to 7 pm it is easier to distinguish different materials and tissue types e.g. constructed of light elements than by using only individual ranges (vision, NIR or X-rays). The invention also concerns a device for conducting the method. Spectral measurements are especially used for generating image date e.g. as images. At least two images are generated of an object that should be examined, and these at least two images constitute coherent images.

The method may consist of determination of an object's reflection in the NIR and/or vision ranges associated with the same object's transmission within the X-rays range, in this way a greater level of details is obtained concerning the construction of the object by determining it surface texture together with a description of its inner structure and/or composition. The method uses generation of images at multispectral electromagnetic waves from at least two ranges within vision (visible light), NIR (near infrared light) and X-rays. It is hereby possible to apply:
- Multispectral vision+multispectral X-rays
- Multispectral NIR+multispectral X-rays
- Multispectral vision+multispectral NIR+multispectral X-rays where multispectral vision can be the entire or parts of the range 700 nm to 350 nm; multispectral NIR can be the entire or parts of the range 950 nm to 700 nm; multispectral X-rays can be the entire or parts of the range 100 pm to 7 pm.

By multispectral is meant that one or more specific frequencies is emitted from each of the described sources or that one or more frequencies is received by the described sensors and where emitted and received frequencies are within any range described herein. The sources may emit electromagnetic waves with larger ranges than the sensors receive or transmit to a processor. The wavelengths received by sensors may be separated by filters to obtain pre-determined wavelengths or pre-determined ranges of wavelengths.

A device suitable for analyzing e.g. food or feed products or waste by simultaneous use of an object's reflection in multispectral NIR and/or multispectral vision associated with the same object's transmission within multispectral X-ray not only has the advantage of combining the two systems of detection reflection of light and transmission of X-rays in one device hereby reducing the production costs of the device and the requirement for space at the point of use instead of acquiring two devices each with only one detection possibility. Also the possibility of analyzing images obtained with reflection in the NIR and/or vision ranges associated with the same object's transmission within the X-ray range may give further information of the scanned objects when compared to analyzing similar objects with only NIR and/or vision or X-rays.

An objects reflection of light when illuminated with multispectral NIR and/or multispectral vision gives information of the structure and/or quality of the illuminated surface of the objects and the multispectral X-ray transmission give information of the objects internal structure and/or quality. By combining the reflection and transmission methods information not only obtained from one of the system may be obtained, some examples are:

Meat pieces with small bone fragments on illuminated surface:
  The bone fragments on the illuminated surface may be detectable by NIR/Vision, however, if the bone fragments are covered with blood the illumination system may not detect the bone fragments as the color of the bone fragments are changed due to the blood,
  X-ray transmission is attenuated by the bone fragments, and hereby the X-ray images can be used in combination with the NIR/vision images to determine whether bone fragments are present on the illuminated surface.

Meat pieces with bone fragments on illuminated or non-illuminated surface:
  If the NIR/vision images indicates bone fragments, the bone fragments are on the illuminated surface, If the NIR/vision images do not indicate bone fragments, and the X-ray images indicate presence of bone fragments the bone fragments may be present on non-illuminated surface.

Trimmings with cartilage:
Cartilage may be indicated in the NIR/vision images and the presence may be confirmed or disconfirmed by X-ray images.

The object which should be examined can be a defined physical item such as individual meat pieces, or it can be a continuous stream of material such as minced meat on a conveyor belt, however, other products can also be examined, preferred is examination of food and feed products. The method make use of establishing coherent measuring results e.g. in the form of coherent image data of reflection and/or transmission in the entire of the object's two-dimensional extent to be able to determine the composition of the object, including being able to scan the object for possible biological materials such as physical symptoms of disease. In respect of continuous streams of material such as minced products e.g. minced meat, the continuous stream of material which preferably is transported on an open conveyor belt is separated into imaginary sections of a predetermined length such that the generated coherent image date become of a size which reflects the predetermined imaginary section. Sub-ranges of the electromagnetic waves may be:

For 950 nm to 700 nm: 950-940, 940-900, 900-860, 860-820, 820-780, 780-740, 740-700, 950-780, 780-700

For 700 nm to 350 nm: 700-660, 660-620, 620-580, 580-540, 540-500, 500-460, 460-420, 420-380, 380-350, 700-620 (red), 620-585 (orange), 585-570 (yellow), 570-490 (green), 490-440 (blue), 440-420 (indigo/violet), 420-400 (violet), 420-400 (violet/UV)

For 100 pm to 7 pm: 100-70, 70-40, 40-7 where any ends in these intervals should be considered flexible especially when using colors to denote a sub-range, as these may be differently sub-divided.

In a preferred embodiment the objects preferably reflection in the NIR- and vision-ranges are combined with the objects transmission in the X-rays range.

Electromagnetic waves in the entire range indicated for each of the three ranges can be used; however it is preferred to use narrower ranges (sub-ranges) within each of the three indicated ranges.

The wavelengths used and detected in the system may be selected based on the type of material to examine. In different embodiments the system may be based on sources emitting electromagnetic waves within the following sub-ranges and detectors detecting electromagnetic waves within the sub-ranges:
Blue: in the range of about 400 to 475 nm, and
X-rays of in the range of about 9-62 pm,
or
Green: in the range of about 500 to 550 nm, and
X-rays of in the range of about 9-62 pm,
or
Red: in the range of about 575 to 700 nm, and
X-rays of in the range of about 9-62 pm,
or
NIR: in the range of about 775 to 950 nm, and
X-rays of in the range of about 9-62 pm,
or
Blue: in the range of about 400 to 475 nm,
Green: in the range of about 500 to 550 nm, and
X-rays of in the range of about 9-62 pm,
or
Blue: in the range of about 400 to 475 nm,
Red: in the range of about 575 to 700 nm, and
X-rays of in the range of about 9-62 pm,
or
Blue: in the range of about 400 to 475 nm,
NIR: in the range of about 775 to 950 nm, and
X-rays of in the range of about 9-62 pm,
or
Green: in the range of about 500 to 550 nm,
Red: in the range of about 575 to 700 nm, and
X-rays of in the range of about 9-62 pm,
or
Green: in the range of about 500 to 550 nm,
NIR: in the range of about 775 to 950 nm, and
X-rays of in the range of about 9-62 pm,
or
Blue: in the range of about 400 to 475 nm,
Red: in the range of about 575 to 700 nm, and
X-rays of in the range of about 9-62 pm,
or
Blue: in the range of about 400 to 475 nm,
NIR: in the range of about 775 to 950 nm, and
X-rays of in the range of about 9-62 pm,
or
Blue: in the range of about 400 to 475 nm,
Green: in the range of about 500 to 550 nm,
Red: in the range of about 575 to 700 nm,
X-rays of in the range of about 9-62 pm,
or
Blue: in the range of about 400 to 475 nm,
Green: in the range of about 500 to 550 nm,
NIR: in the range of about 775 to 950 nm, and
X-rays of in the range of about 9-62 pm,
or
Blue: in the range of about 400 to 475 nm,
Red: in the range of about 575 to 700 nm,
NIR: in the range of about 775 to 950 nm, and
X-rays of in the range of about 9-62 pm,
or
Green: in the range of about 500 to 550 nm,
Red: in the range of about 575 to 700 nm,
NIR: in the range of about 775 to 950 nm, and
X-rays of in the range of about 9-62 pm, In a most preferred embodiment the system is based on sources emitting electromagnetic waves within the following sub-ranges and detectors detecting electromagnetic waves within the following sub-ranges:
Blue: in the range of about 400 to 475 nm,
Green: in the range of about 500 to 550 nm,
Red: in the range of about 575 to 700 nm,
NIR: in the range of about 775 to 950 nm and
X-rays of in the range of about 9-62 pm.

Conversion from photon energy (keV) to photon wavelengths (pm) within the X-ray range is indicated in the table below:

| Photon energy (keV) | Photon wavelength (pm) |
|---|---|
| 7 | 177.4 |
| 12 | 103.5 |
| 20 | 62.1 |
| 40 | 31.1 |
| 60 | 20.7 |
| 90 | 13.8 |
| 100 | 12.4 |

-continued

| Photon energy (keV) | Photon wavelength (pm) |
|---|---|
| 120 | 10.4 |
| 140 | 8.9 |

Figure 5:
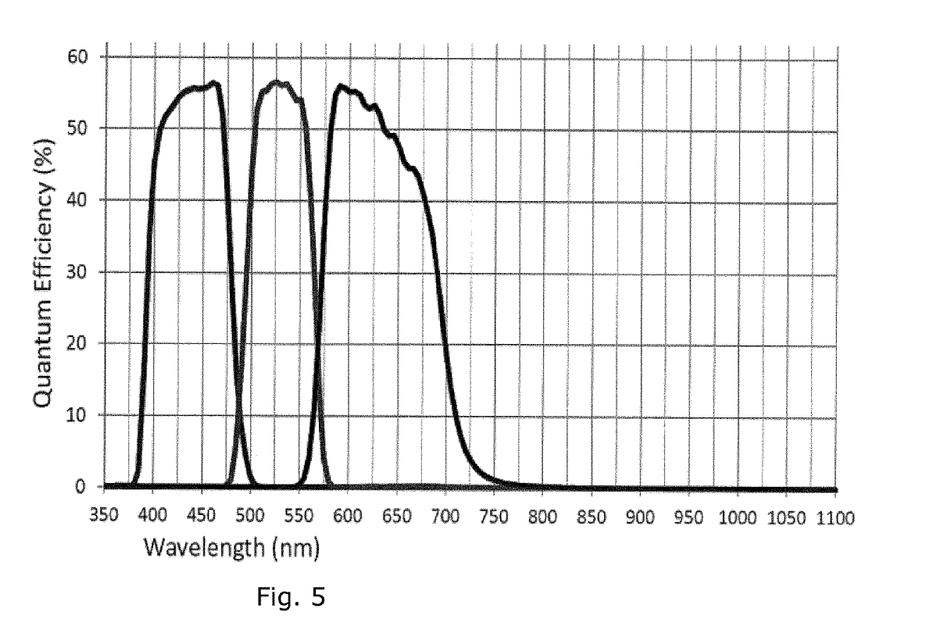
FIG. 5 illustrates the spectral response of the camera JAI Sweep SW-2000T-CXP2.
Figure 6:
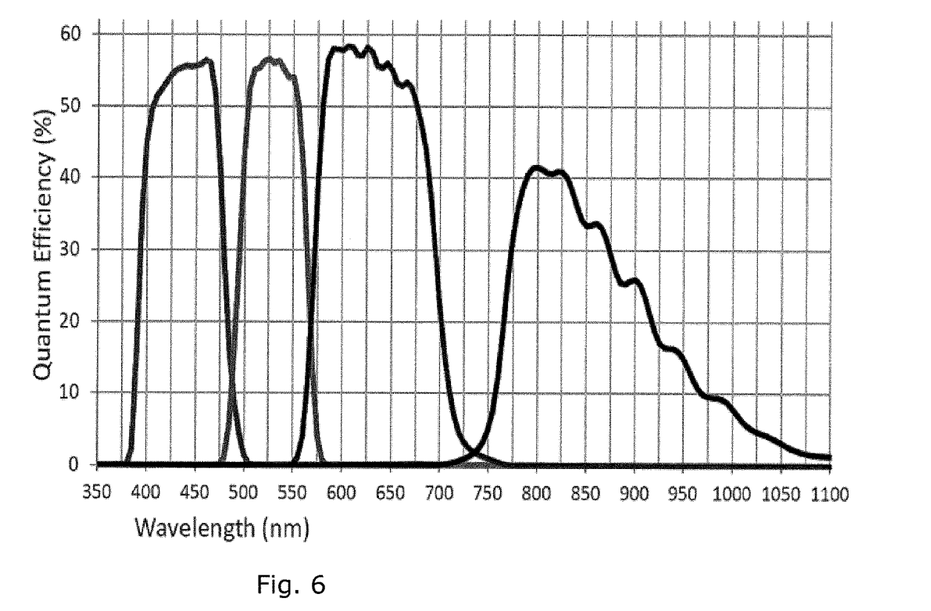
FIG. 6 illustrates the spectral response of the camera JAI Sweep SW-2000Q-CXP2.

Examples of detectors detecting electromagnetic waves may be line scan cameras such as JAI Sweep+ Series: SW-2000T-CL, SW-2000T-CXP2, SW-2000Q-CL, SW-2000Q-CXP2 or similar cameras and updates hereof. FIGS. 5 and 6 indicate the spectral of the cameras SW-2000T-CXP2 and SW-2000Q-CXP2, respectively.

The device for coherent scanning may be constructed with a conveyor belt which move the object in a well-known manner including with a known and uniform velocity between at least two line sensors and/or at least two cameras or a combination of at least one line sensor and at least one camera, each arranged to receive electromagnetic waves in at least one of the ranges 950 nm to 700 nm, 700 nm to 350 nm or 100 pm to 7 pm such that coherent measurements is established of the reflection and transmission in the entire object's two-dimensional extent or imaginary sections of this. By the moving forward of the object by the conveyor band and past the at least two line sensors and/or cameras with a uniform velocity it is possible for each line sensor and/or camera to register data such as image data for the entire object or the imaginary sections of continuous streams of materials and combine this data in layers of e.g. images hereby analyzing the objects two dimensions which faces the line sensors and/or cameras.

In a preferred embodiment of the device the line sensors are produced as one-dimensional arrays of sensors with extension perpendicular to the direction of movement of the conveyor band such that when moving the object translatory past the line sensors it is possible to create a set of coherent 2D-images of the object's reflection and transmission at selected and defined wavelengths in the three ranges.

A set of coherent 2D-images consists of at least two images or two data sets created from input registered by at least two sensors or created from input from at least two in terms of time separate detections by at least one sensor. With the term 'image' means a data set from a single sensor and where data is registered in connection with a single registration of reflection and/or transmission of electromagnetic waves. As the object may be under transport during the scanning process and/or the sensors may be located e.g. with different angles to the object, the algorithms used in the processing and analysis of the images preferably compensate for the movement and/or angling of sensors such that an object area of one image is compared with the same object area of other images although this object area may be shown in different image locations in a sequence of obtained images.

A set of coherent 2D-images may consist of at least three images such as at least four images, e.g. at least five images which are 'added up' or where the entire or parts of at least one image is 'subtracted' from or divided by at least one other image.

Analysis of obtained images may be performed by simultaneously obtaining images of the same part of an object with N different spectral ranges. The images are compared at pixel level with pixels which show the same point of the subject in each image. If analyzing one image for each spectral range the number of analyzed images is N for each pixel. If analyzing more than one image for each spectral range an average may be obtained in each spectral range and the number of image averages is then N for each pixel. For each pixel this may result in an N-dimensional vector with N vector elements, where the vector elements represent the light intensity or X-ray attenuation in that pixel. A processor may compare the N-dimensional vector for a single pixel with a number of pre-determined possibilities to determine what is shown in that pixel. In the images obtained by illumination with NIR and/or vision multispectral ranges the system may when analyzing products obtained from animal carcasses be capable to recognize just about any different structure and may thus be capable to distinguish between light meat, red meat and dark meat as well as tendons, cartilage, bone, white bones etc. The system may also be capable to identify quality deteriorations such as abscesses, excrements, oil etc.

As an example the number of images to be analyzed may be e.g. 128 X-ray images obtained of the same part of an object and obtained at the same time and with different energies/electromagnetic wavelengths together with e.g. 6 NIR and/or vision images also obtained of the same part of an object and obtained at the same time and with different energies/electromagnetic wavelengths. However, the number of X-ray images and NIR and/or vision images may be different.

By reflection and/or transmission of electromagnetic waves will e.g. meat, fat and plastic such as white or blue plastic be able to appear differently in the created images. By adding up images and/or subtracting images, or parts of images are added up/subtracted, coherent 2D-images are created, hereby e.g. plastic can be identified in a meat piece or in a continuous stream of material of animal origin.

The identified plastic may subsequent be removed or the concerned meat piece or a part of the continuous stream of material can be discarded.

In a preferred embodiment of the device the object during its movement on the conveyor belt is illuminated by light-emitting diodes with wavelengths in the range 950 nm to 700 nm and 700 nm to 350 nm and by a tungsten X-ray source with maximum 160 kV accelerating voltage, and an optical line sensor is located above the object and a line sensor sensitive to X-ray energy is located beneath the object such that it is possible due to the knowledge of the uniform velocity of the conveyor band to create at least one set of coherent 2D images of the object's optical reflection spectrum and according to its X-ray transmission spectrum.

In a preferred embodiment the device is equipped with at least one MULTIX ME100 multispectral X-ray detector and at least one JAI Sweep CoaxPress SW-2000Q-CXP2 line camera and LED lighting at least three different wavelengths. Updated versions of the mentioned detector and of the mentioned camera can also be used and/or comparable detectors and sources may be used.

In a preferred embodiment the device is arranged to identify unwanted surface contamination and unwanted internal foreign objects in food.

In a preferred embodiment the device is arranged to identify specific materials in a stream of waste passing through the device on a conveyor belt.

The device and method described herein can e.g. be used to:
  control of food including carcasses or part of carcasses such as meat pieces e.g. for the presence of foreign objects at the surface and/or inside such as plastic and/or metal parts such as parts of needles,
  control of fish e.g. for the presence of foreign objects at the surface and/or inside or to control whether fish bones are removed, control of disintegrated meat pieces such as minced meat and/or fat or meat cut into cubes such as for the presence of foreign bodies at the surface and/or inside, such as plastic, control of processed food such as minced meat or minced meat bound with flour and egg for the presence of foreign bodies at the surface and/or inside, such as plastic, to detect physical disease symptoms at animals especially on carcasses or parts of carcasses, such as pleura scars, abscesses and/or bruises, to detect manure contamination on animals especially on carcasses or parts of carcasses.

An aspect of the invention relates to an equipment for performing scanning of at least one item such as a food or feed item, the equipment may comprise at least two sources for emitting electromagnetic waves selected among sources which can emit electromagnetic waves in a larger or narrower range and where the at least two sources emit electromagnetic waves with waves in different ranges and selected between the ranges
950 nm to 700 nm,
700 nm to 350 nm,
100 pm to 7 pm, Wherein at least one of the sources is capable of emitting electromagnetic waves within at least a part of the range 100 pm to 7 pm, and at least one sensor which can receive electromagnetic waves within part or the entire of at least one of the ranges
950 nm to 700 nm,
700 nm to 350 nm,
100 pm to 7 pm Wherein at least one of the sensors is capable of receiving electromagnetic waves within at least a part of the range 100 pm to 7 pm.

One of the at least two sources preferably emit electromagnetic waves in the range 100 pm to 7 pm and at least one source emit electromagnetic waves within one of the ranges 950 nm to 700 nm and 700 nm to 350 nm.

The at least one sensor is preferably at least two sensors where one sensor can receive electromagnetic waves in the range 100 pm to 7 pm and at least one sensor can receive electromagnetic waves within at least one of the ranges 950 nm to 700 nm and 700 nm to 350 nm.

The sources may be capable of emitting electromagnetic waves in the entire of the described ranges or in any pre-determined sub-range or sub-ranges hereof. Some sub-ranges are described elsewhere herein. The sensors may by capable of receiving electromagnetic waves in the entire of the described ranges or in any pre-determined sub-range or sub-ranges hereof. Preferably, the sensors of an equipment are capable of receiving electromagnetic waves at least with similar wavelengths as can be emitted from the sources of the equipment. Also preferred is that one sensor of the equipment can receive electromagnetic waves within the entire of the ranges 950 nm to 700 nm and/or 700 nm to 350 nm and another sensor of the equipment can receive electromagnetic waves within the entire of the range 100 pm to 7 pm.

The equipment may comprise a computer or processor to which received images/data sets received by the sensors are forwarded. The computer processes the images due to a program or algorithm developed in respect of the product to be scanned and optionally also in respect of the foreign bodies to be detected.

The equipment may further comprise at least one screen located outside of the cabinet and which may be for illustrating one or more scanned products and any foreign bodies being present. The program of the computer may be capable of marking any foreign bodies being present such as encircling the foreign bodies. An alarm may be initialized when a foreign body is detected by the system.

Figure 1:
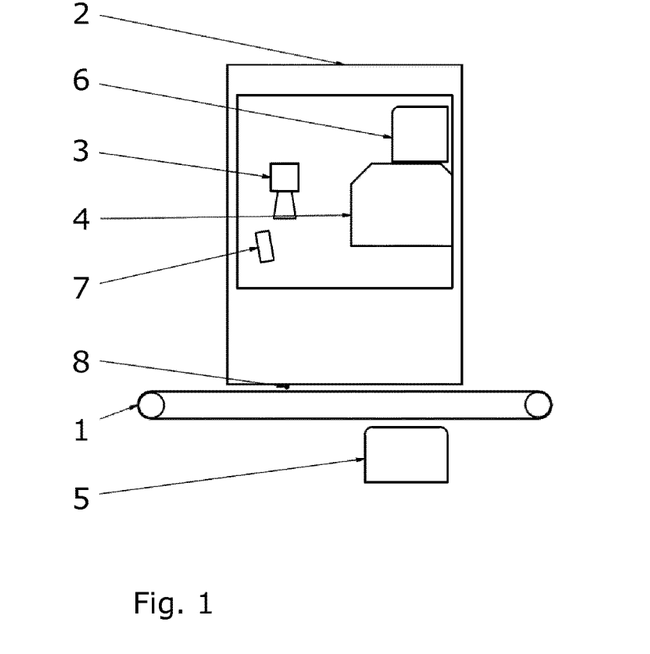
FIG. 1 illustrates a front-view of an open equipment for coherent scanning.

Preferably the location of the sources and sensors are as illustrated in FIG. 1 where sources for emitting electromagnetic waves are located above an area for transporting products such as a conveyor belt and sensor(s) for receiving electromagnetic waves within the ranges 950 nm to 700 nm and/or 700 nm to 350 nm are also located above the area for transporting products whereas sensor(s) for receiving electromagnetic waves within the range 100 pm to 7 pm are located below the area for transporting products. However, the source and sensor(s) for emitting and receiving electromagnetic waves within the range 100 pm to 7 pm may be interchanged i.e. with the X-ray detector located above the area for transporting products.

The equipment may also comprise a conveyor belt, however, the equipment may also be designed to be mounted on a pre-installed conveyor belt in a company where scanning should be performed. As the equipment uses X-rays, the conveyor belt itself should be X-ray penetrable as the X-rays will penetrate the product to be scanned as well as the conveyor belt.

The equipment may also comprise an X-ray non-penetrable closure located at each end of the cabinet such that X-rays do not escape out of the equipment. The non-penetrable closure may be of a flexible material and may be located to close the openings for product transport such that the transported product can pass the closure. A short tunnel may be located at each end of the equipment above the conveyor belt and the closure may be located at the outer end of such tunnels. The tunnels may each have a length corresponding at least to the length of a product to be scanned.

The equipment may further comprise a start sensor located close to and above the conveyor. The start sensor may be located at a location where a scanning of a product under transport should be initiated. This sensor may register when a product to be scanned passes the sensor and may forward information of the presence of a product to the computer/processor which may then control the scanning of the product as long as this product is in the scanning area i.e. in an area where at least some electromagnetic waves reflected or transmitted by the product can be detected by at least one sensor present in the equipment. The start sensor may comprise a visible or non-visible light source and a light sensor, where the light source emits a light beam extending across the conveyor belt and the light sensor register presence and absence of light. When the light beam is interrupted this corresponds to the presence of a product on the conveyor belt and the product can be scanned.

The equipment may further comprise any electric connections to make the electric components function as well as electric data connections between the individual electric parts of the equipment such as between the computer and any of the start sensor, the sources, the sensors, the control panel, and any screen. The computer is preferably pre-programmed to manage each of the electric parts and to process the obtained images.

The equipment may comprise a cabinet enclosing at least the electric components and electric connections between the electric components. The cabinet may be of any suitable material such as steel or polymer. Preferably the cabinet is of steel such as stainless steel which is a suitable material when the equipment is to be used in a company processing food or feed. The cabinet is preferably X-ray absorbing such that X-rays do not escape from the cabinet including the cabinet located beneath the conveyor belt with an X-ray source or an X-ray detector.

The equipment may further comprise a frame structure on which the conveyor belt, the cabinet and the X-ray source or X-ray sensor located below the conveyor belt may be mounted, such that the equipment is a system which can easily be moved. Repositioning of the equipment becomes easier when wheels are mounted on the frame structure at floor level.

The equipment may further comprise at least one opening for light being directed from the at least one source for emitting electromagnetic waves in the ranges of 950 nm to 700 nm and/or 700 nm to 350 nm and towards the product being scanned and for light being emitted (reflected) from the product being scanned and towards the at least one sensor capable of receiving electromagnetic waves in the ranges of 950 nm to 700 nm and/or 700 nm to 350 nm. The opening for light may be located in the bottom part of the equipment below the sources for emitting electromagnetic waves in the ranges of 950 nm to 700 nm and/or 700 nm to 350 nm and below the sensors for receiving electromagnetic waves in the ranges of 950 nm to 700 nm and/or 700 nm to 350 nm and above the conveyor belt. The opening may be a true opening i.e. a hollow opening. For equipment which should be used in areas which should be frequently cleaned the opening may comprise a material penetrable for electromagnetic waves in the ranges of 950 nm to 700 nm and/or 700 nm to 350 nm, this material may be glass, such as laminated glass.

The equipment may further comprise an opening for X-rays, which is located in the bottom part of the equipment below the sources (or sensor if in the reverse construction) for emitting (receiving) electromagnetic waves in the range 100 pm to 7 pm and above the conveyor belt. Such an opening for X-rays need only be necessary if the cabinet is produced of a material interrupting X-rays. For equipment which should be used in areas which should be frequently cleaned the opening for X-rays may comprise a material penetrable for electromagnetic waves in the ranges of 100 pm to 7 pm, this material may be a polymeric material such as POM or PE.

Preferably the equipment comprises a shielding material protecting X-rays from escaping. The X-ray source and X-ray sensor(s) are preferably surrounded by X-ray non-penetrable material.

When the equipment should be used in an area of handling food or feed products, the equipment preferably comprises a hygienic design, such that it is easy to clean and thus reduces the risk of being a place for growth of harmful or undesirable micro-organisms.

The equipment may be pre-installed or may be controlled by a user such that the electromagnetic waves emitted from the sources and electromagnetic waves received by the sensors are determined in respect of the material or item to be scanned and of the foreign body or different object to be identified on and/or in and/or among products.

An equipment may thus comprise sources for emitting electromagnetic waves in few pre-determined ranges of the described ranges, such as red, blue and X-ray and sensors for receiving electromagnetic waves within similar ranges. Another example of sources and sensors of an equipment is red, green, blue, near infrared and X-ray. Yet a further equipment may comprises sources and sensors capable of emitting and receiving NIR, red, orange, yellow, green, blue, violet, UV and X-ray.

The equipment as described herein may comprise a control panel from where a user may select the type of products to be scanned. When selecting the product type on the control panel the computer/processor may pre-programmed to determine which electromagnetic wave sources should be used and thus the wave lengths of emitted electromagnetic waves as well as the wave lengths of received electromagnetic waves received by the sensors. The computer/processor may also be pre-programmed in respect of how the obtained images should be processed to determine any foreign bodies or other structures to be identified on and/or in and/or among the products to be scanned.

The control panel may also give the possibility for the user to select/inform of other facts of the product to be scanned. When scanning e.g. minced meat the information selected on the control panel may be some or all information in respect of whether and what kind of tray the minced meat is located in, the material of the tray, whether the tray is open or closed and if closed by which material, the size of the tray, the amount of minced meat in each tray and the type of minced meat such as which animal race it comes from and type of chopping (fine or coarsely) as well as expected amount of fat and/or meat in the product. For industrial purpose a selection may be reused until changed i.e. until another type of product should be scanned.

For meat products comprising vegetable the system should be informed e.g. by information through the control panel what kind of vegetable is used and how it is processed or is not processed. The computer is preferably pre-programmed to select wave lengths of electromagnetic waves emitted and recorded as well as how to perform an analysis of the obtained images. If the system is not informed of e.g. vegetables or part hereof present in a meat product the vegetables will be identified as foreign bodies.

An aspect of the invention relates to use of the equipment as described herein for analyzing objects. The objects may be any objects suitable to be analyzed within at least the described ranges of wave lengths, such objects may be food or feed products.

A further aspect of the invention relates to use of the method as described herein for analyzing objects. The objects may be any objects suitable to be analyzed within at least the described ranges of wave lengths, such objects may be food or feed products.

Items of the Invention

1. An equipment for scanning materials, where this equipment comprises at least two sources for emitting electromagnetic waves selected among sources which can emit electromagnetic waves in a larger or narrower range and where the at least two sources emit electromagnetic waves with waves in different ranges and selected between the ranges
    950 nm to 700 nm,
    700 nm to 350 nm,
    100 pm to 7 pm,
    And at least one sensor which can receive electromagnetic waves within part or the entire of at least one of the ranges
    950 nm to 700 nm,
    700 nm to 350 nm,
    100 pm to 7 pm.

2. Equipment according to item 1 where the at least two sources are at least three sources and where the at least three source emit electromagnetic waves with wavelengths in different ranges and chosen between the ranges
950 nm to 700 nm,
700 nm to 350 nm,
100 pm to 7 pm.
3. Equipment according to one or more of item 1 and 2, where the at least one sensor is at least two sensors which can receive electromagnetic waves in at least one of the ranges, such as in at least two of the ranges
   i. 950 nm to 700 nm,
   ii. 700 nm to 350 nm,
   iii. 100 pm to 7 pm.
4. Equipment according to one or more of item 1 to 3, where the equipment comprises at least three sources and where the at least three sources emit electromagnetic waves with wavelengths in different ranges, and at least two sensors where one of the sensors can receive electromagnetic waves in at least one of the ranges 950 nm to 700 nm, and 700 nm to 350 nm, and at least one sensor can receive electromagnetic waves in the range 100 pm to 7 pm.
5. Equipment according to one or more of item 1 to 4 where the sources for emitting electromagnetic waves with wavelengths in the ranges 950 nm to 700 nm, and 700 nm to 350 nm and the sensors for receiving electromagnetic waves with wavelengths in the ranges 950 nm to 700 nm, and 700 nm to 350 nm are located such that these sources and sensors when the equipment is in function are located at the same side of an object which should be examined, such that these sensors detect reflection of electromagnetic waves from an object.
6. Equipment according to one or more of item 1 to 5 where the sources for emitting electromagnetic waves with wavelengths in the range 100 pm to 7 pm and the sensors for receiving electromagnetic waves with wavelengths in the range 100 pm to 7 pm are located such that these sources and sensors when the equipment is in function are located on opposite sides of an object which should be examined, such that these sensors detect transmission of electromagnetic waves in an object.
7. Equipment according to one or more of item 1 to 6 further comprising at least one conveyor belt for transporting objects which should be examine, where at least sources that emit electromagnetic waves with wavelengths in the ranges 950 nm to 700 nm, and 700 nm to 350 nm and sensors for receiving electromagnetic waves with wavelengths in the ranges 950 nm to 700 nm, and 700 nm to 350 nm are located above the conveyor belt when this transports objects which should be examined and where sources which emit electromagnetic waves with wavelengths in the ranges 100 pm to 7 pm are located opposite of sensors for receiving electromagnetic waves with wavelengths in the ranges 100 pm to 7 pm.
8. Equipment according to item 7 where the sensors for receiving electromagnetic waves with wavelengths in the range 100 pm to 7 pm are located with at least one source at one side of the conveyor belt and at least one sensor at the opposite side of the conveyor belt.
9. Equipment according to one or more of item 1 to 8, where at least one sensor comprises at least one line sensor such as at least two line sensors, where the at least one line sensor can be one-dimensional array of sensors.
10. Equipment according to one or more of item 9, where the at least one line sensor has an extension perpendicular to the transport direction of the conveyor belt.
11. Equipment according to one or more of item 9, where the equipment have at least two line sensors located with a distance of at least 5 cm seen in relation to the transport direction of the objects such as the transport direction on the conveyor belt.
12. Equipment according to one or more of item 1 to 11 further comprising at least one device for transferring input from the at least one sensor to a processor for processing data such as for creating a set of coherent 2D-images of the object's reflection and/or the object's transmission at predetermined and defined wavelengths.
13. Equipment according to one or more of item 1 to 12 further comprising means for analyzing constructed 2D-images such as for giving an alarm if material with a unwanted reflection and/or transmission is identified among the scanned objects.
14. A method for scanning objects, where electromagnetic waves within at least two selected ranges of electromagnetic waves is emitted towards an object which should be examine, and where the at least two selected ranges of electromagnetic waves are electromagnetic waves with waves in different ranges and selected between the ranges
950 nm to 700 nm,
700 nm to 350 nm,
100 pm to 7 pm,
And detection of the electromagnetic which is reflected or transmitted of the object within part or the entire of at least one of the ranges
950 nm to 700 nm,
700 nm to 350 nm,
100 pm to 7 pm.
15. The method according to claim 14, wherein at least three selected ranges of wavelength is emitted towards the object which should be examined and where the at least three ranges of wavelengths are electromagnetic waves with wavelengths in different areas and selected within at least three of the ranges
950 nm to 700 nm,
700 nm to 350 nm,
100 pm to 7 pm.
16. The method according to one or more of item 14 to 15, where detection is of reflection or transmission of electromagnetic waves in at least two of the ranges:
950 nm to 700 nm,
700 nm to 350 nm,
100 pm to 7 pm.
17. The method according to one or more of item 14 to 16, where electromagnetic waves emitted towards the object and become detected as reflected or transmitted have wavelengths selected within the ranges 950 nm to 700 nm, 700 nm to 350 nm, and 100 pm to 7 pm such that each of the ranges is represented as emitted and detected range.
18. The method according to one or more of item 14 to 17, where electromagnetic waves is emitted towards at least one object and reflected and/or transmitted electromagnetic waves is detected while this object is transported on a conveyor belt.

19. The method according to one or more of item 14 to 17, where electromagnetic waves reflected and/or transmitted by at least one of the objects is detected from at least two angles and/or with time related intervals.
20. The method according to one or more of item 14 to 17, where the registered data in the form of electromagnetic waves reflected and/or transmitted of at least one object is processed to creation of at least one set of coherent 2D-images of the object's reflection and/or the object's transmission at selected and defined wavelengths.
21. The method according to one or more of item 14 to 17, where the surface texture of the at least one object and/or its inner composition is determined.
22. The method according to one or more of item 14 to 17, where the at least one object is a foodstuff or waste.
23. The method according to one or more of item 14 to 17, where the at least one object is checked for unwanted foreign bodies such as unwanted surface decontamination and/or unwanted inner foreign bodies.

DETAILED DESCRIPTION OF THE FIGURES

FIG. 1 illustrates a front-view of an open equipment for coherent scanning. When in function the opening will be closes and the closure may comprise a control panel. The system is illustrated with a conveyor belt (1) which conveys the product to be analyzed through the scanning system. The main part of the scanning system is located above the conveyor belt (1) within a cabinet (2). Illustrated is a start sensor (8) which will register the presence of a product on the conveyor belt and the scanning will be performed, a light source (7) emitting electromagnetic waves of pre-determined wave length(s) towards the product to be scanned, a camera (3) which recognizes light of pre-determined wave lengths and an X-ray source (4) emitting X-rays and a X-ray detector (5) located below the conveyor belt (1). Shown is also a possible position for a computer (6) located within the cabinet (2).

In the figure it is indicated that the conveyor belt (1) runs in both directions between the cabinet (2) and the X-ray detector (5), however, preferably the X-ray detector (5) is located in between i.e. under the part transporting the products to be scanned and above the returning part of the conveyor belt. Rollers may be located to direct the returning part of the conveyor belt (1) below the X-ray detector (5).

Figure 2:
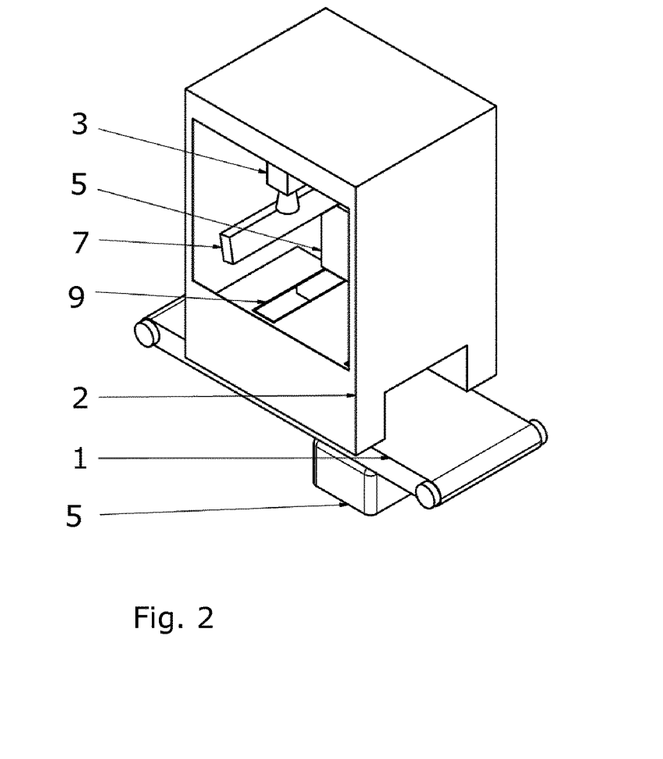
FIG. 2 illustrates an angled view from above of an open equipment for coherent scanning.

FIG. 2 illustrates an angled view from above of an open equipment for coherent scanning. Shown in the cabinet (2) are a camera (3), an X-ray source (4) emitting X-rays and a X-ray detector (5) located below the conveyor belt, a light source (7) emitting electromagnetic waves of pre-determined wave length(s), which electromagnetic waves will pass the 9. Opening for light (9) and reflected light will return through the opening for light (9). The light source (7) emitting electromagnetic waves of pre-determined wave length(s) is indicated as an elongated light source and the light emitted may be emitted as lines along substantially the entire length of the light source (7) and thus also along substantially the entire length of the opening for light (9).

Figure 3:
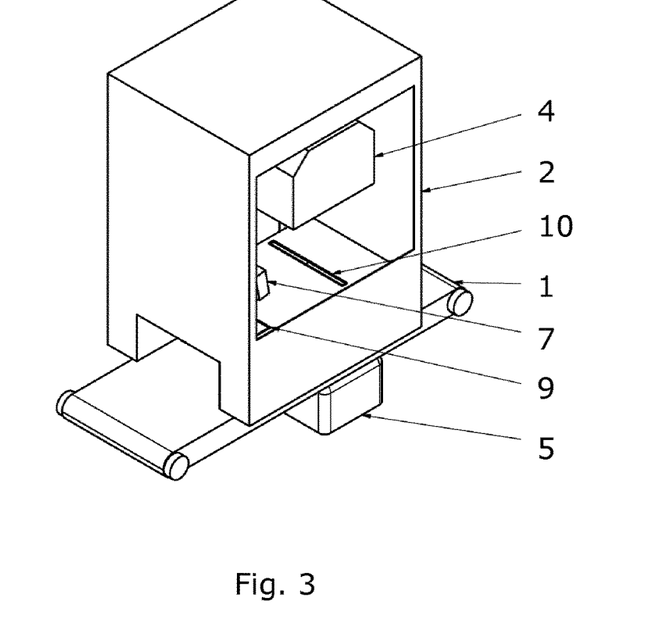

FIG. 3 illustrates an angled view from above of an open equipment for coherent scanning. Indicated is a conveyor belt (1) for transporting objects to be scanned. Above the conveyor belt (1) are a cabinet (2) with a light source (7) emitting electromagnetic waves of pre-determined wave length(s) towards the product to be scanned, an opening for light (9), an X-ray source (4) emitting X-rays which passes an opening for X-rays (10), the product to be scanned (not shown) and through the conveyor belt to an X-ray detector (5) located below the conveyor belt (1).

Figure 4:
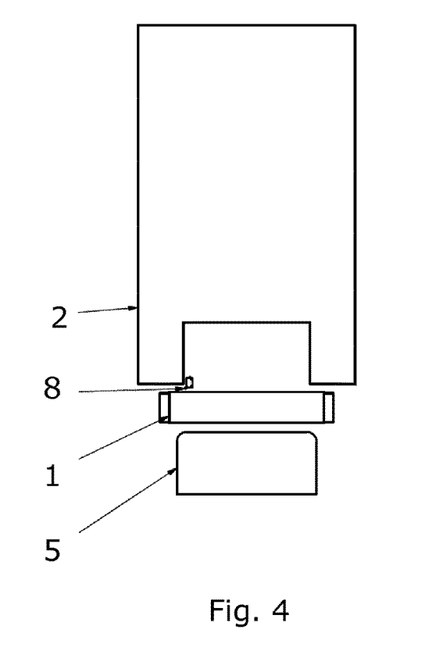
FIG. 4 illustrates a side-view of an equipment for coherent scanning.

FIG. 4 illustrates a side-view of an equipment for coherent scanning. Illustrated are a conveyor belt (1), a cabinet (2), a start sensor (8) and an X-ray detector (5) located below the conveyor belt (1).

FIG. 5 illustrates the spectral response of the camera JAI Sweep SW-2000T-CXP2. The camera detects blue, green and red colors in the sub-ranges of about 400 to 475 nm (blue), 500 to 550 nm (green), and 575 to 700 nm (red).

FIG. 6 illustrates the spectral response of the camera JAI Sweep SW-2000Q-CXP2. The camera detects blue, green and red colors as well as NIR electromagnetic waves. The camera detects blue, green and red colors together with NIR in the sub-ranges of about 400 to 475 nm (blue), 500 to 550 nm (green), 575 to 700 nm (red), and 775 to 950 nm (NIR).

LIST OF REFERENCE SIGNS

In the figures, identical structures, elements or parts that appear in more than one figure are generally labeled with the same numeral in all the figures in which they appear.
1. Conveyor belt
2. Cabinet
3. Sensor(s) for receiving electromagnetic waves such as camera(s)
4. X-ray source
5. X-ray detector
6. Computer/processor
7. Sources for emitting electromagnetic waves such as light source(s)
8. Start sensor
9. Opening for light
10. Opening for X-rays

The invention claimed is:

1. An equipment for scanning and analyzing materials, where the equipment comprises:
   at least two sources configured to emit electromagnetic waves in different ranges, wherein the different ranges are selected from a group consisting of: a first range from 950 nm to 700 nm, a second range from 700 nm to 350 nm, and a third range from 100 pm to 7 pm; wherein at least one of the sources is configured to emit the electromagnetic waves within at least a part of the third range; and
   at least one sensor configured to receive the electromagnetic waves within part of or an entirety of at least one of the first range, the second range, or the third range; wherein at least one of the sensors is configured to receive the electromagnetic waves within at least a part of the third range.

2. The equipment according to claim 1, wherein a first subset of one or more of the at least two sources are configured to emit the electromagnetic waves with wavelengths in the first range or the second range, and a first set of one or more of the at least one sensor is configured to receive the electromagnetic waves with wavelengths in the first range or the second range; and wherein the first set of one or more of the at least two sources and the first set of one or more of the at least one sensor are located on a same side of an object under examination when the equipment is in function, such that the first set of one or more of the at least one sensor detects a reflection of the electromagnetic waves from the object; and
   a second set of one or more of the at least two sources is configured to emit the electromagnetic waves with wavelengths in the third range and a second set of one or more of the at least one sensor is configured to receive the electromagnetic waves with wavelengths in the third range; and wherein the second set of one or more of the at least two sources and the second set of one or more of the at least one sensor are located on opposite sides of the object under examination when the equipment is in function, such that the second set of one or more of the at least one sensor detects a transmission of the electromagnetic waves through the object.

3. The equipment according to claim 2, further comprising:
at least one conveyor belt configured to transport the object under examination;
where the first set of one or more sources of the at least two sources and the first set of one or more sensors of the at least one are located above the conveyor belt when the conveyor belt transports the object under examination; and
where the second set of one or more sources of the at least two sources are located opposite the second set of one or more sensors of the at least one sensor.

4. The equipment according to claim 3, where the at least one sensor comprises at least one line sensor, where the at least one line sensor is a one-dimensional array of sensors comprising an extension perpendicular to a transport direction of the conveyor belt.

5. The equipment according to claim 3, where the equipment comprises at least two line sensors located within a distance of at least 5 cm, from a transport direction of the object under examination.

6. The equipment according to claim 1, further comprising:
at least one device configured to transfer input from the at least one sensor to a processor configured to process data to create a set of coherent 2D-images of the reflection of the electromagnetic waves from the object or the transmission of the electromagnetic waves through the ohiect at defined wavelengths.

7. The equipment according to claim 6, further comprising:
an alarm configured to trigger an alert when material with an unwanted reflection or transmission is identified among the object under examination based at least in tart on an analysis of the 2D-images.

8. A method for scanning and analyzing objects, comprising:
emitting electromagnetic waves within at least two different ranges towards an object under examination, and where the at least two different ranges are selected from a group consisting of: a first range from 950 nm to 700 nm, a second range from 700 nm to 350 nm, and a third range from 100 pm to 7 pm, wherein at least one of the different ranges is within at least a part of the third range; and
detecting a reflection of the electromagnetic waves from the object or a transmission of the electromagnetic waves through the object within at least a portion of the at least two ranges wherein the at least a portion of the at least two ranges comprises at least a portion of the third range.

9. The method according o claim 8, further comprising:
detecting the reflection of the electromagnetic waves or the transmission of the electromagnetic waves from sat least two angles or within time related intervals.

10. The method according to claim 8, further comprising:
processing registered data corresponding to the detected reflection the electromagnetic waves or the detected transmission of the electromagnetic waves to create at least one set of coherent 2D-images of the detected reflection of the electromagnetic waves or the detected transmission of the electromagnetic waves at defined wavelengths.

11. The method according to claim 10, further comprising:
obtaining the at least one set of 2D-images by simultaneously obtaining at least two images of the same part of the object.

12. The method according to claim 10, further comprising:
performing a pixel analysis of the at least one set of 2D-images by comparing pixels from different images related to a point of the object to determine what is shown in the compared pixels.

13. The method according to claim 8, further comprising:
transporting the object during the scanning by a conveyor belt.

* * * * *